United States Patent [19]

Dunphy et al.

[11] Patent Number: 5,493,113

[45] Date of Patent: Feb. 20, 1996

[54] HIGHLY SENSITIVE OPTICAL FIBER CAVITY COATING REMOVAL DETECTION

[75] Inventors: James R. Dunphy, South Glastonbury; James J. Ryan, Windsor Locks, both of Conn.

[73] Assignee: United Technologies Corporation, Hartford, Conn.

[21] Appl. No.: 346,104

[22] Filed: Nov. 29, 1994

[51] Int. Cl.⁶ .................................. G01J 4/00; G01J 5/08
[52] U.S. Cl. .................. 250/227.19; 250/227.14; 250/227.23; 250/227.27; 356/345; 385/13
[58] Field of Search ................. 250/227.14, 227.18, 250/227.23, 227.19, 227.27, 231.19, 237 G; 385/12, 13; 356/345

[56] References Cited

U.S. PATENT DOCUMENTS

| | | | |
|---|---|---|---|
| 4,725,110 | 2/1988 | Glenn et al. | 350/3.61 |
| 4,761,073 | 8/1988 | Meltz et al. | 356/32 |
| 4,970,385 | 11/1990 | Tatsuno et al. | 250/225 |
| 5,202,939 | 4/1993 | Belleville et al. | 385/12 |
| 5,351,324 | 9/1994 | Forman | 385/37 |
| 5,359,681 | 10/1994 | Jorgenson et al. | 385/12 |
| 5,361,130 | 11/1994 | Kersey et al. | 356/345 |
| 5,394,488 | 2/1995 | Fernald et al. | 385/13 |
| 5,399,854 | 3/1995 | Dunphy et al. | 250/227.17 |
| 5,401,956 | 3/1995 | Dunphy et al. | 250/227.18 |

*Primary Examiner*—Edward P. Westin
*Assistant Examiner*—Stephen Calogeno
*Attorney, Agent, or Firm*—Gerald L. DePardo

[57] ABSTRACT

A highly sensitive optical fiber cavity coating removal detector employs an optical fiber 18 having a pair of Bragg gratings 20,30 embedded therein and separated by a section of fiber making up an optical cavity 26. The optical path length of the cavity 26 is sized with the central reflection wavelength of the fiber gratings 20,30 so as to create an optical resonator. The cavity 26 is coated with a material 40 which corrodes or is otherwise removable, such as aluminum. The coating 40 exerts forces 46 radially inward on the cavity 26 so as to cause the refractive index of the cavity and thus its optical path length to change, thereby causing the resonator to come out of resonance. The forces 46 on the cavity 26 are reduced when the coating 40 corrodes, thereby causing the resonator to re-enter resonance. Additionally, the coating causes optical losses to exist due to non-uniform variations in refractive index caused by non-uniform forces from coating irregularities.

11 Claims, 1 Drawing Sheet

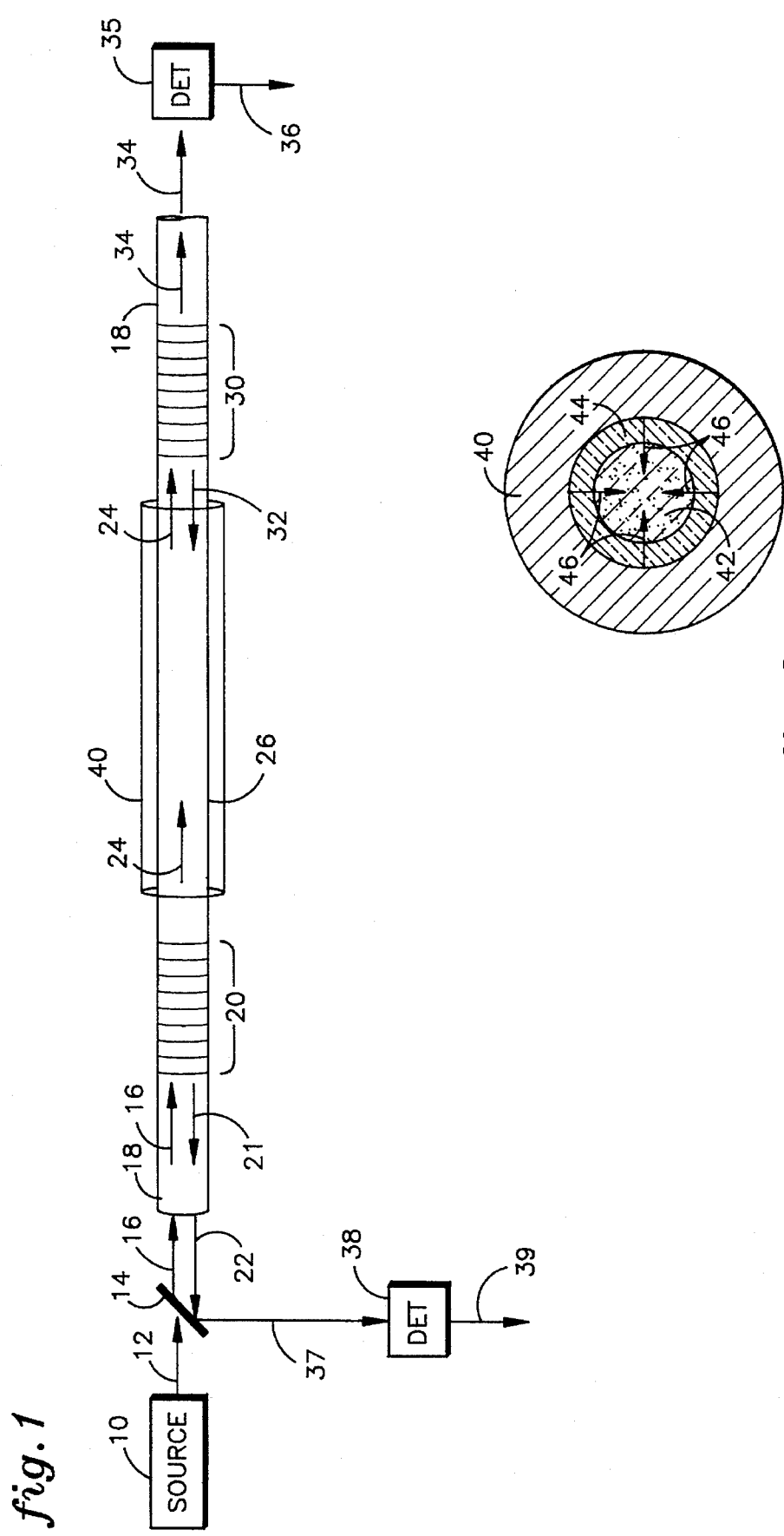

HIGHLY SENSITIVE OPTICAL FIBER CAVITY COATING REMOVAL DETECTION

CROSS REFERENCES TO RELATED APPLICATIONS

Copending U.S. patent application Ser. No. 08/346,059, entitled "Optical Fiber Bragg Grating Coating Removal Detection", filed contemporaneously herewith, contains subject matter related to that disclosed herein.

TECHNICAL FIELD

This invention relates to smart structures and more particularly to optical corrosion detection.

BACKGROUND ART

It is known in the field of optical temperature and strain sensor technology to distribute sensors along a surface of or within a surface of a structure. Such sensors provide information about the stresses induced at various points on the structure, thereby providing information regarding fatigue, lifetime, and maintenance repair cycles of the structure. Such sensor-integrated structures and the optics and electronics that make them functional are known as "smart structures." One such system is described in copending U.S. patent application Ser. No. 08/207,993, entitled "Embedded Optical Sensor Capable of Strain and Temperature Measurement."

In addition to measuring stresses and temperatures at various points in a structure, it is also desirable to ascertain information regarding corrosion of structural components to determine when the structure is unfit for its normal use. For example, if corrosion occurs at critical stress points along the fuselage or wings of an airplane, structural failure may result.

Thus, it is desirable to obtain a sensor capable of detecting corrosion in structural materials.

SUMMARY OF INVENTION

Objects of the invention include provision of an optical sensor which detects corrosion.

According to the present invention, an optical sensor includes an optical fiber making up an optical cavity; a pair of reflective fiber gratings embedded within the optical fiber, each grating having a central reflection wavelength, delimiting the optical cavity; the optical path length and propagation losses of the cavity being sized together with the central reflection wavelengths of the fiber gratings so as to create an optical resonator; a coating of a material having a predetermined thickness and being around the circumference and along the length of the cavity; the coating exerting forces radially inward on the cavity so as to cause a change in the overall refractive index of the cavity, thereby causing the optical path length of the cavity to change and causing the resonator to come out of resonance; and the forces on the cavity being reduced when the coating is at least partially removed, thereby causing the resonator to enter resonance.

According further to the present invention, the forces from the coating are non-uniformly distributed around and along the cavity causing variations in refractive index of the cavity thereby reducing the optical efficiency of the cavity.

The invention represents an advancement in smart structure technology which allows for the detection of corrosion in structures by the discovery that a fiber waveguide optical cavity coated with a material, such as aluminum, exhibits changes in optical path length and optical waveguiding characteristics. The invention is lightweight, inexpensive, and easy to install and has high sensitivity to corrosion. Furthermore, the sensor is easily coupled with other smart sensor technology such as temperature and/or strain sensors which also use fiber Bragg gratings. Still further, the use of a resonator cavity for such detection allows for extremely sensitive detection.

The foregoing and other objects, features and advantages of the present invention will become more apparent in light of the following detailed description of exemplary embodiments thereof as illustrated in the accompanying drawings.

BRIEF DESCRIPTION OF DRAWINGS

FIG. 1 is a drawing showing an optical fiber coated with an aluminum coating between two fiber Bragg gratings making up a resonator cavity, in accordance with the present invention.

FIG. 2 is a cross-sectional view of an optical fiber showing a core, a cladding, and an aluminum coating, in accordance with the present invention.

BEST MODE FOR CARRYING OUT THE INVENTION

Referring to FIG. 1, a light source 10 provides an optical signal 12 to a beam splitter 14, which passes a predetermined amount of light 16 into an optical fiber 18. The light 16 is incident on a first fiber Bragg grating 20 embedded within the fiber 18. A fiber Bragg grating, as is known, reflects a narrow wavelength band of light and passes all other wavelengths, thereby exhibiting a narrow wavelength reflectivity profile, as is discussed in U.S. Pat. No. 4,725,110 to Glenn et al. The grating 20 reflects a narrow wavelength band of light 21 and passes the remaining wavelengths as indicated by a line 24. The light 24 travels along a section of fiber 26 to a second grating 30, embedded within the fiber 18, which reflects a narrow wavelength band of light 32 and passes the remaining wavelengths as indicated by a line 34. The light 34 exits the fiber 18 and is incident on a detector 35 which provides an electrical signal on a line 36 indicative of the intensity of the light 34 incident thereon. Similarly, output light 22 exits the grating resonator pair 20,30 (discussed hereinafter) along the optical fiber 18 and is incident on the beam splitter 14 which reflects a predetermined amount of light 37 onto a detector 38. The detector 38 provides an electrical signal 39 indicative of the intensity of the light 37 incident thereon. Also, the section fiber 26 is surrounded by a coating 40 made of, e.g., aluminum (methods for coating are discussed hereinafter).

Referring now to FIG. 2, a cross-section of the section 26 of the optical fiber 18 comprises an optical core 42 made of germania-doped silica having a diameter of about 6–9 microns. Surrounding the core 42 is a fiber cladding 44 made of pure silica having an outer diameter of about 125 microns. Surrounding the cladding 44 is the aluminum coating 40 having an outer diameter of approximately 196 microns. Other materials and diameters for the core, cladding, and coating may be used, if desired, provided they are consistent with the operation and performance requirements associated with optical fiber resonators.

The aluminum coating 40 induces radial pressure (or forces) directed radially inward as indicated by lines 46 on the fiber cladding 44 and the fiber core 42. The overall average pressure from the coating 40 causes an overall average change in the effective index of refraction n of the section 26 of fiber, thereby affecting the optical path length between the two gratings 20,30.

The gratings 20,30 are matched to provide a peak reflectivity at the same central reflection wavelength, thereby creating an optical resonator cavity in the section 26 of the fiber 18 between the two gratings 20,30. This cavity may be used as a Fabry-Perot resonator which has a high finesse or high-Q narrow wavelength-band resonator response. The two gratings 20,30 and the resonator cavity 26 operate as an optical resonator provided the central reflectivity wavelength of the gratings 20,30 and the optical path length of the cavity 26 are precisely set to provide an optical resonance, as is known. Further, resonator performance can be optimized by minimizing the optical losses between the gratings (discussed hereinafter).

When an optical resonance exists, the transmitted output light beam 34 (viewing the resonant cavity 26 and gratings 20,30 as resonator system) exhibits a peak at the resonance frequency (or wavelength), as is known, and the output light 22 exhibits a minimum due to the complementary relationship between the output light beams 22,34. Conversely, when an optical resonance exists such that the output light beam 22 exhibits a peak at the resonance frequency (or wavelength), the output light 34 will be a minimum, as is also known. Due to the narrow wavelength bandwidth of the resonator, any small change in optical path length between the gratings 20,30 will cause a significant decrease in the intensity of the output light 34 at the resonant wavelength. Therefore, the resonator is designed to resonate without the coating 40 applied to the fiber 26. Then, when the coating 40 is applied, the overall average pressure from the coating 40 causes a change in the average refractive index of the fiber 26, as discussed hereinbefore. As a result, the optical path length changes from that required for a resonance to occur and causes the output intensity at the resonant wavelength to be greatly decreased (i.e., the resonator comes out of resonance).

As corrosion occurs, the pressure caused by the coating 40 decreases and the optical path length returns to its previously uncoated value. Consequently, the optical resonance is exhibited (i.e., the cavity re-enters resonance), the output light intensity at the resonance wavelength increases, and the output signals from the detectors 35,38 increase.

If the coating is only partially removed, i.e., the coating is merely thinned or is removed only in some areas but not others, a corresponding change in the resonator response toward an uncoated cavity will result. The amount of coating removal needed before the cavity will exhibit a change depends on the initial force applied to the cavity by the coating, the stiffness of coating material, and the thickness of the coating remaining, and can be easily determined by those skilled in the art.

Alternatively, if the resonator is designed to resonate with the coating 40 applied, then, as corrosion occurs, the pressure is reduced, and the optical path length of the cavity changes, the system will come out of resonance and the power of the output light at the resonance wavelength will greatly decrease.

Also, as the radial pressure 46 exerted by the coating 40 changes, the physical length L of the section 26 of fiber also changes based on Poisson's ratio, as is known. This effect attributes to the overall change in optical path length. However, this effect is quite small relative to the other effects discussed hereinbefore.

Additionally, the thickness of the coating 40 around the circumference of the cladding 44 is not perfectly uniform and the thickness of the coating 40 along the longitudinal axis (or length) of the fiber 26 is also not perfectly uniform. As a result, the coated fiber experiences a non-uniform random variation of the pressure 46 (called "microbends") which causes a non-uniform random variation in the refractive index of the cavity 26. Consequently, the light 24,32 within the cavity 26 experiences losses or inefficiency in propagation between the gratings 20,30 when the coating 40 exists (i.e., prior to corrosion), and thereby changing the Q (or finesse) of the resonator. Therefore, optical losses in the resonator cavity will likely be greatest when a coating exists around the cavity. Consequently, the lowest loss resonant cavity design exists when the resonator is designed to resonate with an uncoated cavity.

As discussed hereinbefore, whether the cavity is in resonance, or not in resonance, is related to the optical path length (or index of refraction) which is related to the overall average force exerted by the coating on the fiber cavity. Also, as discussed hereinbefore, the optical cavity propagation losses (or inefficiencies) are caused by the aforementioned microbends (or non-uniform forces applied to the cavity). As a result, we have found that the process used for coating the cavity and the type of coating material used, determines the amount of change in optical path length and the amount of optical loss which occurs in the resonator.

Accordingly, if the fiber is coated with aluminum when the fiber is at the melting temperature of aluminum, e.g., by dipping the fiber into molten aluminum at temperature of about 650° C. then removing the fiber to facilitate cooling and adhesion of the coating to the surface of the fiber, the large difference in thermal expansion coefficients between fiber and aluminum cause a large overall force to be exerted on the fiber during cooling which causes a large change in the average refractive index of the cavity. This technique is known as "freeze coating."

However, if the fiber is maintained substantially at ambient temperature during the coating process (e.g., by sputtering or by vapor deposition), the cooling temperature gradient for the fiber is not as large and, thus, the overall average force exerted on the fiber is not as large as the previously discussed dipping technique. Accordingly, the average refractive index change and the associated change in optical path length is smaller. Also, when using such a process, the coating tends to be quite smooth and uniform. As such, the non-uniform forces or microbends discussed hereinbefore are less and, thus, the amount of optical losses are less than the aforementioned dipping technique.

Therefore, we have found that it is possible to tailor the amount of change in refractive index (and the associated change in optical path length) by adjusting the amount of overall average force applied to the cavity, which is directly related to the temperature of the fiber during coating and the thermal expansion coefficient of the coating material. Also, it is possible to tailor the amount of optical loss along the cavity by adjusting the smoothness and uniformity of the coating applied to the cavity.

The invention provides for extremely sensitive detection of coating removal. In particular, it is known that sensors based on optical resonators, such as fiber Fabry-Perot interferometers, can detect disturbance-induced phase shifts as small as a few microradians (fractions of a degree). As such, changes in phase ($\Delta\phi/\phi$) of approximately $10^{-5}$ radians can be detected. It is also known that the phase shift along an optical fiber (which is directly related to a change in optical path length) may be calculated as:

$$\Delta\phi/\phi = \Delta L/L + \Delta n/n \qquad [\text{eq. 1}]$$

where $\Delta L$ is the disturbance-induced change in physical path length L and $\Delta n$ is the disturbance-induced change in the average effective core refractive index n. This phase shift can be rewritten in terms of the dominant components associated with disturbance-induced longitudinal strain $\epsilon_z$ and radial strain $\epsilon_r$ imposed on the optical fiber such that:

$$\Delta\phi/\phi = 0.7\,\epsilon_z + 0.4\,\epsilon_r \qquad [\text{eq. 2}]$$

As discussed hereinbefore, the process of freeze coating an optical fiber with a material such as aluminum imposes transverse radial pressure and longitudinal stresses that create radial and longitudinal strain components. These coating-induced strain components can generate a significant phase shift on the order of about $10^{-3}$ radians. Therefore, the invention is capable of detecting very small (e.g., less than 1%) corrosion-induced changes in the aluminum coating properties when an optical resonator is used as discussed herein.

Instead of using a pure Fabry-Perot resonator-type cavity 26, the section of fiber 26 may instead be doped with a predetermined dopant to create a fiber laser. Such a fiber laser is discussed in U.S. Pat. No. 5,305,335 to Ball et al entitled "Single Longitudinal Mode Pumped Optical Waveguide Laser Arrangement." When using the invention in a fiber laser configuration, similar design constraints are imposed as for the aforementioned resonator design. In particular, the appropriate optical path length is critical for lasing to occur. Such optical path length can be designed together with the reflection wavelengths of the gratings to cause lasing to occur when the coating is not applied. When the cavity, or some portion of the cavity, is then coated, the optical path length changes and lasing is reduced or does not occur. Then when corrosion occurs, the optical path length returns to its previously uncoated state and lasing occurs (or increases in intensity) and the output light will exhibit an intensity peak at the lasing wavelength. Alternatively, the fiber laser may be designed so as to lase when the coating is applied, thereby causing the output light to decrease at the lasing wavelength, and/or to exhibit a shift in the lasing wavelength, when corrosion occurs.

It should be understood that the source 10 may be a broadband light source and the detector 38 may be an optical spectrometer which provides an electrical signal 39 indicative of the wavelength reflectivity profile, i.e., the reflected wavelengths and the associated intensities thereof. Alternatively, the source may be a variable source such as that described in copending U.S. patent application, Ser. No. 08/129,217, entitled "Diagnostic System for Fiber Grating Sensors." Other configurations may be used if desired to detect the changes in the optical output signals due to corrosion. Any other means of analyzing the optical output signals 22 or 34 (depending on whether the device is operating in reflection or transmission) may be used to detect the changes in the optical output signals due to corrosion.

Furthermore, a material other than aluminum may be used as the coating around the cavity, provided such coating either corrodes, evaporates, thins, or in some other way is removed partially of completely from coating the cavity so as to reduce the forces exerted on the cavity. Therefore, the invention may be used to detect the partial or complete removal of any coating surrounding a cavity, provided a predetermined criteria of changes in overall average force and non-uniformity of forces on the grating are satisfied, as discussed hereinbefore.

Also, instead of applying the coating to the entire length of the cavity, only a portion of the cavity length may be coated.

Although the invention has been described and illustrated with respect to the exemplary embodiments thereof, it should be understood by those skilled in the art that the foregoing and various other changes, omissions and additions may be made without departing from the spirit and scope of the invention.

We claim:

1. An optical sensor, comprising:

an optical fiber making up an optical cavity;

a pair of reflective fiber gratings embedded within said optical fiber, each grating having a central reflection wavelength, delimiting said optical cavity;

the optical path length and propagation losses of said cavity being sized together with the central reflection wavelengths of said fiber gratings so as to create an optical resonator;

a coating of a material having a predetermined thickness and being around the circumference and along the length of said cavity;

said coating exerting forces radially inward on said cavity so as to cause a change in the overall refractive index of said cavity, thereby causing the optical path length of said cavity to change and causing the resonator to come out of resonance; and said forces on said cavity being reduced when said coating is at least partially removed, thereby causing the resonator to enter resonance.

2. The sensor of claim 1 wherein said optical fiber comprises a fiber core and a cladding surrounding said fiber core.

3. The sensor of claim 1 wherein said cavity comprises a gain medium, thereby making a laser cavity.

4. The sensor of claim 1 wherein said forces from said coating are non-uniformly distributed around and along said cavity causing variations in refractive index of the cavity thereby reducing the optical efficiency of said cavity.

5. The sensor of claim 1 wherein said coating comprises aluminum.

6. The sensor of claim 1 wherein the removal of said coating comprises corrosion of said coating.

7. A method for making an optical sensor, comprising:

obtaining an optical fiber making up an optical cavity having a pair of reflective fiber gratings embedded within said optical fiber, each having a central reflection wavelength, delimiting said optical cavity;

sizing the optical path length and propagation losses of said cavity together with the central reflection wavelengths of said fiber gratings so as to create an optical resonator;

applying a coating to said cavity around the circumference of and along the length of said cavity;

said coating exerting forces radially inward on said cavity so as to cause a change in the overall refractive index of said cavity, thereby causing the optical path length of said cavity to change and causing the resonator to come out of resonance; and said forces on said cavity being reduced when said coating is at least partially removed, thereby causing the resonator to enter resonance.

8. The method of claim 7 wherein said coating comprises aluminum.

9. The method of claim 7 wherein said step of applying said coating comprises vapor deposition.

10. The method of claim 7 wherein said step of applying said coating comprises freeze coating.

11. The method of claim 7 wherein the removal of said coating comprises corrosion of said coating.

* * * * *